United States Patent [19]

Kunimune et al.

[11] Patent Number: 4,609,700
[45] Date of Patent: Sep. 2, 1986

[54] SOLUBLE IMIDE OLIGOMER AND A METHOD FOR PRODUCING THE SAME

[75] Inventors: Kouichi Kunimune, Ichiharashi; Shiro Konotsune, Yokosukashi, both of Japan

[73] Assignee: Chisso Corporation, Osaka, Japan

[21] Appl. No.: 732,726

[22] Filed: Jun. 19, 1985

[51] Int. Cl.[4] .............................................. C08K 5/34
[52] U.S. Cl. .................... 524/104; 524/173; 524/233; 524/588; 528/26; 528/41
[58] Field of Search ............... 528/41, 26; 524/104, 524/233, 173, 588

[56] References Cited

U.S. PATENT DOCUMENTS

| | | | |
|---|---|---|---|
| 3,883,486 | 5/1975 | Bargain | 525/422 |
| 4,064,193 | 12/1977 | Bargain | 525/421 |
| 4,472,565 | 9/1984 | Ryang | 528/26 |

*Primary Examiner*—Melvyn I. Marquis
*Attorney, Agent, or Firm*—Fred Philpitt

[57] ABSTRACT

A soluble imide oligomer represented by the general formula

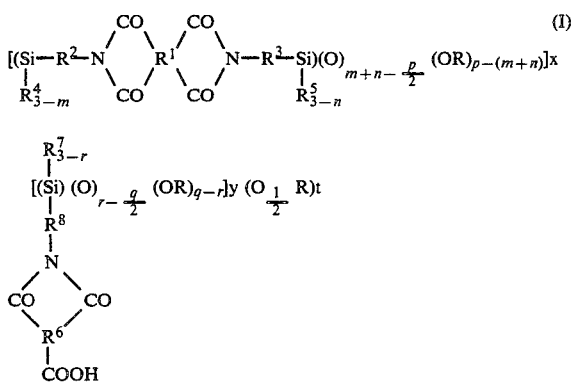

(Definitions of R, $R^1$, $R^2$, $R^3$, $R^4$, $R^5$, $R^6$, $R^7$ and $R^8$ are found in the specification.) and its preparation process are presented. A coating solution for electronic materials containing said soluble imide oligomer is also presented.

25 Claims, 1 Drawing Figure

FIG. 1

SOLUBLE IMIDE OLIGOMER AND A METHOD FOR PRODUCING THE SAME

BACKGROUND OF THE INVENTION

1. Field of Art

This invention relates to a novel precursor of a silicon-containing polyimide polymer, a method for preparing the same, and a use of the same.

As protective and insulating materials in the field of electronics, polyimide resins have been widely used mainly from the viewpoint of their heat-resisting properties. From the overall point of view, however, they are not always satisfactory in this field with not a few points to be improved. In general, a precursor of polyimide for electronic materials is coated, in the form of a polyamic acid solution, on a base material, and baked to form a cured imide product. Such a coating solution has extremely high viscosity, leading to a drawback of poor workability. Furthermore, such a precursor has other drawbacks that baking thereof requires so high temperatures, e.g., 300° to 400° C., so as to exceed the temperature of heat resistance of the base material, and that adhesion thereof to an object to be coated therewith, such as a silicon wafer or glass, is insufficient.

2. Prior Arts

A number of copolymers of polyimide precursors with silicon compounds have been proposed for the improvement of adhesion. For example, Japanese Patent Application Laid-Open Specifications No. 143,328 (1982), No. 7,473 (1983) and No. 13,631 (1983) have proposed polyimidesiloxane copolymers which are obtained by replacing a part of a diamine as a raw material with a polysiloxane terminated with diamine molecules at both the ends thereof. However, this case involves drawbacks that the heat-resisting properties of cured products formed from these copolymers are reduced with increasing siloxane contents in the copolymers, and that copolymerization of the diamine with the polysiloxane entails lowering of the polymerization degree of the resulting polyamic acid, leading to poor film forming properties.

Japanese Patent Publications No. 32,162 (1983), and No. 32,163 (1983) disclose polyamide carboxylic acids and the like including amic acids usable in the present invention. However, these polyamide carboxylic acids and the like have a drawback that baking thereof into imides requires high temperature of at least 300° C. as in the case of conventional polyamide carboxylic acids. These pieces of patent literature further disclose cyclization (imide formation) carried out chemically by a treatment with a dehydrating agent under mild condition. However, the cyclization according to this treatment requires a long time, and the resultant cyclized products have a drawback that those having Si contents are inferior in film forming properties due to low viscosities in the form of varnishes thereof attributed to low molecular weights thereof, while those having low Si contents are inferior in adhesion of cured products therefrom to a silicon wafer or glass.

It is, therefore, an object of the present invention to provide a polyimide-siloxane prepolymer which are suitable for use in surface protecting films for semiconductors and in insulating films between multi-layer wiring layers, soluble in an adequate solvent, capable of being cured by baking at relatively low temperature, which provides good workability when made into a solution and good film-forming properties, and which provides good adhesion of a cured product therefrom to a silicon wafer, glass, and the like.

SUMMARY OF THE INVENTION

In accordance with one aspect of the present invention, there is provided a soluble imide oligomer having an inherent viscosity of 0.05 to 0.5 dl/g, and represented by a general formula (I) mentioned below.

In accordance with another aspect of the present invention, there is provided a process for preparing a soluble imide oligomer of the kind as defined above, which comprises reacting an amic acid compound represented by a general formula (II) mentioned below, or a mixture thereof with 10 mole % or less of an amic acid compound represented by a general formula (III) mentioned below, in the presence of 70% by weight or more, based on a solution, of a solvent, at a temperature of 60°~200° C. for 0.2~6 hours, and, if necessary, in the additional presence of $\{(m+n-2)x+(r-1)y\}$ mole or less, per mole of the above-mentioned amic acid compound or mixture, of water at a temperature of 60° to 200° C. for 0.2 to 6 hours.

In accordance with still another aspect of the present invention, there is provided a coating solution for electronic materials comprising a solvent and 30% by weight or less, based on the total of said solvent and the following oligomer, of a soluble imide oligomer of the kind as defined above.

In the above-mentioned formulae (I), (II) and (III), $R^1$ and $R^6$ are tetravalent and trivalent carbocyclic aromatic groups, respectively, carbonyl groups in carboxyl, amide and imide groups being bonded to the carbocyclic aromatic groups at the mutually different ring-forming carbon atoms thereof, every pair of imide ring-forming carbonyl groups being bonded to a carbocyclic ring of the carbocyclic aromatic groups in the mutual ortho positions thereof; $R^2$, $R^3$ and $R^8$, which are the same or different groups, are (wherein s is an integer of 1 to 4); $R^4$, $R^5$ and $R^7$, which are the same or different groups, are an alkyl group having 1 to 6 carbon atoms, a phenyl group, or an alkyl-substituted phenyl group having 7 to 12 carbon atoms; X is an alkoxyl group, an acetoxyl group, a halogen atom, or a hydroxyl group; R is hydrogen or alkyl or acetyl group derived from X; m and n each are an integer of 1, 2 or 3, and satisfy an equation: $m+n \geq 3$; r is 2 or 3; p and q are integers and satisfy the relation of $m+n \leq p < 2(m+n)-1$ and $r \leq q < 2r-1$; t is 0 or 2; and m and y correspond to relative amounts (by mole) of the amic acid compounds reacted, and satisfy an equation;

$$0 \leq \frac{100 \, y}{x+y} \leq 10.$$

The above-mentioned inherent viscosity is "$\eta$ inh" represented by the following equation:

$$\eta \text{ inh} = \frac{\ln \eta/\eta_0}{C}$$

wherein $\eta$ is a value as measured using an Ubbellohde viscometer at a sample concentration of 0.5 g/dl in a solvent, N-methyl-2-pyrrolidone, at a temperature of $30\pm0.01°$ C., $\eta_0$ is a value for the solvent, N-methyl-2-pyrrolidone, as measured using the same viscometer at the same temperature, and C represents the sample concentration of 0.5 g/dl.

As examples of the above-mentioned $R^1$, can be mentioned and as examples of the above-mentioned $R^4$, $R^5$ and $R^7$, $-CH_3$, $-C_2H_5$ and can be mentioned.

Examples of the compound represented by the general formula (II) and to be used in the process of the present invention include the following compounds.

-continued

-continued

These amic acid compounds can be prepared, for example, by reacting a tetracarboxylic dianhydride with amino silicon compounds, respectively represented by general formulae (IV) and (V) mentioned below:

$$NH_2-R^2-SiR^4{}_{3-m}X_m \qquad (IV)$$

$$NH_2-R^3-SiR^5{}_{3-n}X_n \qquad (V)$$

wherein $R^2$, $R^3$, $R^4$, $R^5$, X, m and n have the same meanings as defined before. In the reaction, the amino silicon compounds of the formulae (IV) and (V) may be either the same or different.

As an example of the above-mentioned $R^6$, can be mentioned.

Examples of the compound represented by the general formula (III) and to be used in the process of the present invention include the following compounds.

These amic acid compounds can be prepared, for example, by reacting a tricarboxylic acid anhydride with an amino silicon compound represented by a general formula (VI) mentioned below.

$$NH_2-R^8-SiR^7{}_{3-r}X_r \qquad (VI)$$

wherein $R^7$, $R^8$, $X$ and $r$ have the same meanings as defined before.

The imide oligomer compound of the present invention may be synthesized by reacting the aforementioned amic acid compound (II), or compounds (II) and (III) in the presence of a solvent as mentioned later under the specifically controlled conditions.

If the aforementioned amic acid compound (III) is involved in the synthesis, the imide oligomer according to the present invention provides improved adhesion to a metal when it is coated on the metal. The compound (III) content of the reaction system is preferably 10% by mole or less based on the total amount of the compounds (II) and (III). Too high a compound (III) content may disadvantageously result in poor film forming properties of an imide oligomer to be obtained. When the compound (III) content of the reaction system is about 0.1% by mole or more based on the total amount of the compounds (II) and (III), there appears a marked effect on improvement in adhesion of the imide oligomer according to the present invention to a metal. However, any content of the compound (III) lower than the above-mentioned is permissible for the purpose of the present invention.

Specific examples of the reaction solvent include N-methyl-2-pyrrolidone, dimethylacetamide, dimethylformamide, dimethyl sulfoxide, tetramethylurea, pyridine, dimethylsulfone, hexamethylphosphoric amide, methylformamide, N-acetyl-2-pyrrolidone, toluene, xylene, ethylene glycol monomethyl ether, and ethylene glycol monoethyl ether. They may be used either alone or in combination. A mixed solvent of 30 to less than 100% by weight of at least one of these solvent with at least one different solvent may also be used. The specifically controlled reaction conditions mentioned before will be explained as follows. An amic acid compound of the general formula (II), or a combination of amic acid compounds of the respective general formulae (II) and (III) is dissolved in the above-mentioned solvent. The amic acid concentration is preferably 30% by weight or less. When the concentration exceeds 30% by weight, there is a fear of formation of some non-dissolved imide compound though it depends on the conditions. The lower limit of the amic acid compound concentration should be determined with the procedure of using the resultant product and the economical viewpoint being taken into consideration. The lower limit is preferably about 2% by weight.

The reaction temperature is preferably 60° to 200° C. Temperatures of less than 60° C. may allow the reaction to proceed, but sometimes leads to uneconomical result. A temperature exceeding 200° C. is unnecessary. A reaction time of 0.2 to 6 hours is satisfactory.

When the reaction is carried out under the conditions as described above, the amic acid compound of the general formula (II), or the amic acid compounds of the general formulae (II) and (III) are subjected to dehydration to form an imide oligomer compound.

If X in the foregoing formulae is a hydrolizable group such as an alkoxy group, hydrolysis, occurs with water formed by the imide formation reaction, followed by condensation to form siloxane linkages allowing polymerization to proceed. Too much increased a molecular weight of the product entails insolubilization thereof in the solvent. On the contrary, when hydrolysis and condensation reactions are not allowed to proceed, an imide oligomer compound having no or poor film forming properties is obtained. More specifically, a soluble imide oligomer having good film forming properties can be obtained only under the controlled reaction conditions in accordance with the process of the present invention. An imide formation reaction promoting agent such as a tertiary amine may be added to the reaction system, but is not always required. This is because, in the case of X being a hydrolizable group, water formed by imide formation reaction is immediately consumed for hydrolysis of X under the reaction conditions adopted in the present invention to enable the imide formation reaction to proceed mildly but rapidly as compared with the usual imide formation reactions. This is one feature of the process of the present invention.

The hydrolysis reaction can be promoted with the aid of an acid catalyst or the like, which may, however, give a bad influence when remained after the reaction. In view of this, if the hydrolysis reaction insufficiently proceeds, the reaction is preferably allowed to proceed with addition of $\{(m+n-2)x+(r-1)y\}$ mole or less, per mole of the amic acid compound(s), of water, without addition of any acid catalyst subsequently to the reaction (having been carried out under the condition without addition of water) at the same temperature and for the same time. Thus the desired imide oligomer can be obtained.

The imide compound of the present invention thus synthesized is an oligomer having an inherent viscosity of 0.05 to 0.5 dl/g as measured under the following conditions.

$$\text{Inherent Viscosity } \eta \text{ inh} = \frac{\ln \eta/\eta_0}{C}$$

The measurement is carried out using an Ubbellohde viscometer at a sample concentration of 0.5 g/dl in a solvent of N-methyl-2-pyrrolidone, at a temperature of $30 \pm 0.01°$ C. Herein, $\eta$ and $\eta_0$ are viscosities of a sample solution of 0.5 g/dl in concentration and the solvent, respectively, and C represents the sample concentration of 0.5 g/dl.

In the case of an imide compound of less than 0.5 dl/g in inherent viscosity, a coating solution thereof is not satisfactory in film forming properties. On the other hand, such an imide oligomer compound as has an inherent viscosity exceeding 0.5 dl/g cannot be measured with respect to accurate inherent viscosity because of poor solvent solubility thereof.

If F is substituted for and G is substituted for HOOC one part of the oligomer of the present invention can be expressed for example as follows;

(R: acetyl, alkyl or hydrogen)

In case the imide oligomer compound of the present invention is used in the form of a coating solution for electronic materials, it may, according to need, be rid of any ionic compounds by adsorption with a solid adsorbent, or other procedure, and/or of minute solid impurities with filtration with a filter of 0.5 μm or less in mesh size. The aforementioned reaction solvent may be used as the solvent of the coating solution, too. The imide oligomer concentration of the coating solution may be determined depending on the desired thickness of a coated film, but is preferably 30% by weight or less, more preferably 0.3 to 25% by weight, based on the total of the solvent and the oligomer, from the practical point of view. Such an imide oligomer concentration as exceeds 30% by weight based on the total of the solvent and the oligomer disadvantageously results in poor flowability. Besides the compound of the general formula (I), the coating solution may additionally comprise an oligomer apparently represented by the same formula as the general formula (I) but defined with such different meanings of x and y in the formula as satisfies the equation: $100y/(x+y) > 10$ (including a case of $x=0$). Also in this case, the amount of the compound of the formula (III) is preferably 10% by mole or less based on the total amount of the compounds of the formulae (II) and (III) in order not give harmful effect upon insulating property. The coating solution may be uniformly coated on a silicon wafer, a glass plate or other material according to any customary procedure, for example, using a spinner, followed by baking to form a hard film. The baking conditions may be more or less different depending on the solvent used, the thickness of a film formed and the like. A baking temperature of 100° to 300° C., and a baking time of 0.5 to 1.5 hours are satisfactory.

The merits of the present invention will be specifically described. A coating solution for electronic materials which contains the imide oligomer compound according to the present invention is compared with a conventional coating solution of a precursor of polyimide. Since it contains a polymer of an amic acid, the latter solution requires a high baking temperature, is subject to a large change with time, and presents a difficulty in handling due to its high viscosity. On the other hand, since the coating solution according to the present invention contains a compound already subjected to an imide formation reaction, the baking temperature thereof may be low as compared with that of the conventional coating solution, and the handling thereof is easy due to low viscosity of the solution, which can be attributed to a low molecular weight of the oligomer compound. Furthermore, since the oligomer compound contains many siloxane linkages, a coated film formed from the coating solution according to the present invention has good adhesion to a base material such as a silicon wafer or glass.

An imide oligomer according to the present invention synthesized using an amic acid compound of the general formula (III) as a part of the raw materials has improved adhesion to metals such as copper, aluminum, etc., and, hence, a highly practical merit.

With respect to heat resisting properties, a coated film formed from a coating solution containing the reaction product of only aromatic amic acid compound(s) according to the present invention is never inferior to a coated film formed from the conventional coating solution comprising only other aromatic polyamic acid(s). Furthermore, the coated film formed from the coating solution according to the present invention turned out to be capable of being widely changed in surface hardness depending on the kind of amic acid compound(s) chosen as the raw material(s).

As described above, great industrial merits can be gained by providing the compound of the present invention having a variety of excellent properties and the process of the present invention for preparing the same easily and efficiently.

PREFERRED EMBODIMENTS OF THE INVENTION

The following Examples illustrate the present invention in connection with the merits thereof in more detail, but should not be construed as limiting the scope thereof.

REFERENCE EXAMPLE 1

A 1 l flask equipped with an agitator, a dropping funnel, a thermometer and a nitrogen replacement means was set in cool water. After the atmosphere in the flask was replaced with nitrogen, 500 ml of N-methyl-2-pyrrolidone as dehydrated and purified and 185.58 g (0.838 mole) of 3-aminopropyltriethoxysilane were put into the flask, followed by agitation. 91.42 g (0.419 mole) of pyromellitic dianhydride in the form of a powder was put into the dropping funnel, from which the powder was fallen inside the flask little by little over 30 minutes to continue a reaction. During the 30 minutes' period, the reaction temperature was maintained in the range of 0° to 5° C. After that, the temperature was raised to 20° to 25° C., in which range the reaction was continued for one hour. A nearly colorless and transparent liquid was obtained.

A part of the reaction mixture solution was sampled and dried under room temperatures and reduced pressures. The light-brown substance thus obtained was subjected to infrared absorption spectroscopic analysis. Absorption peaks assigned to amide appeared at 3,280 cm$^{-1}$ and 1,550 cm$^{-1}$, while an absorption peaks at 1,490 cm$^{-1}$ assigned to amine in a raw material compound disappeared. An absorption peak at 1,780 cm$^{-1}$ assigned to carbonyl in pyromellitic dianhydride as another raw material compound shifted to 1,720 cm$^{-1}$. These clearly indicate formation of an amic acid compound.

REFERENCE EXAMPLE 2

Using the same equipment and substantially the same procedure as in Reference Example 1, 85.19 g (0.399 mole) of p-aminophenylmethoxysilane and 43.56 g (0.200 mole) of pyromellitic dianhydride were reacted in 500 ml of n-methyl-2-pyrrolidone as the solvent at 5° to 15° C. for one hour and at 20° to 25° C. for further one hour.

As a result of infrared absorption spectroscopic analysis of the reaction product, formation of an amic acid compound was confirmed in the same manner as in Reference Example 1.

REFERENCE EXAMPLE 3

Using the same equipment and substantially the same procedure as in Reference Example 1, 82.02 g (0.429 mole) of 3-aminopropylmethyldiethoxysilane and 46.73 g (0.214 mole) of pyromellitic dianhydride were reacted in 500 ml of N-methyl-2-pyrrolidone as the solvent at 0° to 10° C. for one hour and at 20° to 25° C. for further two hour.

As a result of infrared absorption spectroscopic analysis of the reaction product, formation of an amic acid compound was confirmed in the same manner as in Reference Example 1.

REFERENCE EXAMPLE 4

Using the same equipment and substantially the same procedure as in Reference Example 1, 82.50 g (0.460 mole) of 3-aminopropyltrimethoxysilane and 74.17 g (0.0230 mole) of 3,3',4,4'-benzophenonetetracarboxylic dianhydride were reacted in 500 ml of N,N-dimethylacetamide at 5° to 10° C. for one hour and at 25° to 30° C. for further two hour.

As a result of infrared absorption spectroscopic analysis of the reaction product, formation of an amic acid compound was confirmed in the same manner as in Reference Example 1.

REFERENCE EXAMPLE 5

Using the same equipment and substantially the same procedure as in Reference Example 1, 79.73 g (0.360 mole) of 3-aminopropyltrimethoxysilane and 39.27 g (0.180 mole) of pyromellitic dianhydride were reacted in 500 ml of N,N-dimethylformamide at 0° to 5° C. for one hour and at 20° to 25° C. for further one hour.

As a result of infrared absorption spectroscopic analysis of the reaction product, formation of an amic acid compound was confirmed in the same manner as in Reference Example 1.

REFERENCE EXAMPLE 6

Using the same equipment and substantially the same procedure as in Reference Example 1, 68.93 g (0.311 mole) of 3-aminopropyltriethoxysilane and 59.82 g (0.311 mole) of trimellitic dianhydride were reacted in 500 ml of N-methyl-2-pyrrolidone at 5° to 10° C. for one hour and at 25° to 30° C. for further three hours.

As a result of infrared absorption spectroscopic analysis of the reaction product, formation of an amic acid compound was confirmed in the same manner as in Reference Example 1.

Subsequently, imide oligomers according to the present invention were synthesized using the amic acid compounds prepared in Reference Examples, in some of the following Examples, which will give better understanding of the invention in conjunction with the accompanying drawing in which.

EXAMPLE 1

A 100 ml flask equipped with an agitator, a thermometer and a nitrogen replacement means was set in a constant temperature bath. After the atmosphere in the flask was replaced with nitrogen, 14.29 g of the 35% by weight solution of the amic acid compound synthesized in Reference Example 1 and 35.71 g of N-methyl-2-pyrrolidone were put into the flask to prepare 50 g of a 10% by weight solution. The solution thus prepared was subjected, with agitation, to a reaction at 150° C. for 3 hours. A light-yellow and transparent liquid was obtained.

Figure 1:
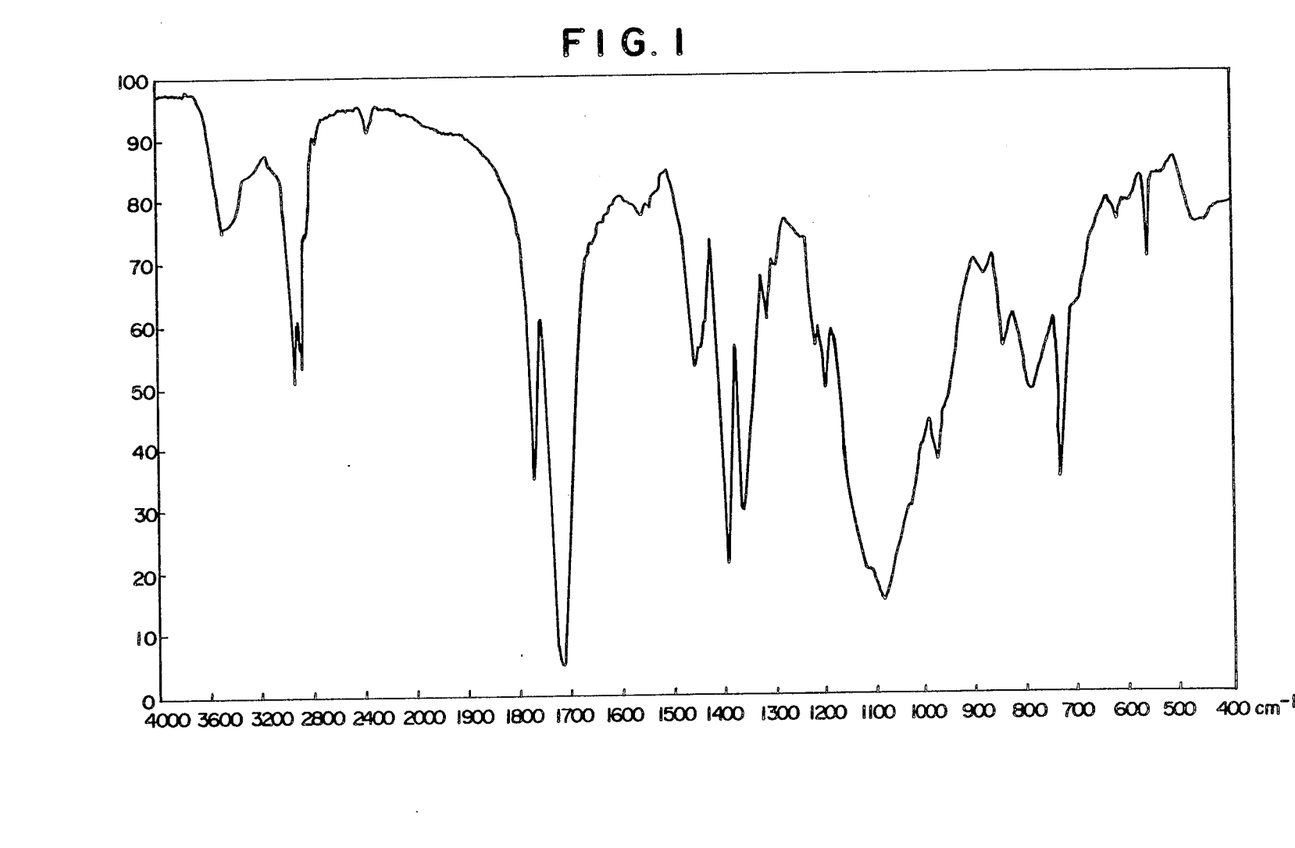
FIG. 1 is an infrared absorption spectra chart for an imide oligomer according to the present invention, which was prepared in Example 1.

A part of the reaction mixture solution was sampled and dried under room temperature and reduced pressures. A light-brown solid thus obtained was subjected to infrared absorption spectroscopic analysis. The chart obtained is shown in FIG. 1, from which it is apparent that absorption peaks at 3,280 cm$^{-1}$ and 1,550 cm$^{-1}$ assigned to amide disappeared while new peaks at 1,780 cm$^{-1}$ and 720 cm$^{-1}$ assigned to imide ring appeared. This clearly indicates that the amic acid compound was dehydrated to form an imide compound. The inherent viscosity ($\eta$ inh) of this compound was 0.21 dl/g.

COMPARATIVE EXAMPLE 1

Using the same equipment and substantially the same procedure as in Example 1, 50 g of the 35% by weight solution of the amic acid compound synthesized in Reference Example 1 was subjected, without further dilution with any solvent, to a reaction carried out by gradually raising the temperature from room temperatures. 40 minutes after start of heating, when the temperature reached 140° C., the solution was gelled and lost its flowability.

COMPARATIVE EXAMPLE 2

Using the same equipment and substantially the same procedure as in Example 1, 50 g of a 10% by weight solution was prepared from 14.29 g of the 35% by weight solution of the amic acid compound synthesized in Reference Example 1 and 35.71 g of N-methyl-2-pyrrolidone. The solution thus prepared was subjected, in the presence of 1.0 g of pyridine as a catalyst and 2.0 g of acetic anhydride as a dehydrating agent for promoting imide formation, to a reaction at 40° C. for 10 hours.

As a result of infrared absorption spectroscopic analysis, the compound thus obtained was confirmed to be an imide compound. The inherent viscosity of this compound was 0.022 dl/g.

EXAMPLE 2

Using the same equipment and substantially the same procedure as in Example 1, 50 g of the 20% by weight solution of the amic acid compound synthesized in Reference Example 2 was as such subjected to a reaction at 80° C. for 3 hours. A light-brown and transparent liquid was obtained.

As a result of infrared absorption spectroscopic analysis of the reaction product, formation of an imide compound was confirmed. The inherent viscosity of this compound was 0.083 dl/g.

EXAMPLE 3

Using the same equipment and substantially the same procedure as in Example 1, 50 g of a 5% by weight solution was prepared from 12.5 g of a 20% by weight solution of the amic acid compound synthesized in Reference Example 3 and 37.5 g of N-methyl-2-pyrrolidone. The solution thus prepared was subjected, with addition of 0.25 g of water for promoting hydrolysis, to a reaction at 180° C. for 5 hours.

As a result of infrared absorption spectroscopic analysis, the compound thus obtained was confirmed to be an amide compound. The inherent viscosity of this compound was 0.39 dl/g.

EXAMPLE 4

Using the same equipment and substantially the same procedure as in Example 1, 50 g of the 25% by weight solution of the amic acid compound synthesized in Reference Example 4 was as such subjected to a reaction at 60° C. for 5 hours.

As a result of infrared absorption spectroscopic analysis, the compound thus obtained was confirmed to be an imide compound. The inherent viscosity of this compound was 0.22 dl/g.

EXAMPLE 5

Using the same equipment and substantially the same procedure as in Example 1, 50 g of a 10% by weight solution was prepared from 25 g of the 20% by weight solution of the amic acid compound synthesized in Reference Example 5 and 25 g of methyl cellosolve. The solution thus prepared was subjected to a reaction at 100° C. for 3 hours.

As a result of infrared absorption spectroscopic analysis, the compound thus obtained was confirmed to be an imide compound. The inherent viscosity of this compound was 0.13 dl/g.

EXAMPLE 6

Using the same equipment as used in Example 1, substantially the same procedure as in Example 1 was repeated. More specifically, 13.90 g of the 35% by weight solution of the amic acid compound synthesized in Reference Example 1, 0.68 g of the 20% by weight solution of the amic acid compound synthesized in Reference Example 6, and 35.42 g of N-methyl-2-pyrrolidone were put into the flask to prepare 50 g of a solution having a total amic acid compounds concentration of 10% by weight and a proportion of the amic acid compound represented the general formula (III) prepared from trimellitic acid anhydride and 3-aminopropyltriethoxysilane, relative to the total amic acid compounds, of 5.0% by mole, which was then subjected, with agitation, to a reaction at 100° C. for 5 hours. A light-yellow and transparent liquid was obtained.

As a result of infrared absorption spectroscopic analysis of the reaction product, formation of an imide compound was confirmed. The inherent viscosity of this compound was 0.078 dl/g.

EXAMPLE 7

The following coating tests were conducted. The reaction mixture solutions prepared in Reference Examples, Examples and Comparative Examples were filtrated with a 0.2 μm filter, and coated on glass plates, followed by baking at 100° to 300° C. for one hour. The states of coated films thus formed were observed.

The results are shown in Table 1.

TABLE 1

| Run No. | Coating Solution | Baking Temperature 100° C. | 200° C. | 300° C. | State of Coated Film |
|---|---|---|---|---|---|
| 1 | Reference Example 1 | x | x | x | A film was not formed. |
| 2 | Reference Example 2 | Δ | Δ | x | A film was formed by baking at 100 to 200° C., but poor in strength. |
| 3 | Reference Example 3 | Δ | Δ | x | A film was formed by baking at 100 to 200° C., but poor in strength. |
| 4 | Reference Example 4 | x | x | x | A film was not formed. |
| 5 | Reference Example 5 | x | x | x | " |
| 6 | Reference Example 6 | x | x | x | " |
| 7 | Comparative Example 2 | x | x | x | " |
| 8 | Example 1 | o | o | o | A sufficiently strong film was formed by baking at 100 to 300° C. Its adhesion to a glass plate was good. |
| 9 | Example 2 | o | o | o | A sufficiently strong film was formed by baking at 100 to 300° C. Its adhesion to a glass plate was good. |
| 10 | Example 3 | o | o | o | A sufficiently strong film was formed by baking at 100 to 300° C. Its adhesion to a glass plate was good. |
| 11 | Example 4 | o | o | o | A sufficiently strong film was formed by baking at 100 to 300° C. Its adhesion to a glass plate was good. |
| 12 | Example 5 | o | o | o | A sufficiently strong film was formed by baking at 100 to 300° C. Its adhesion to a glass plate was good. |
| 13 | Example 6 | o | o | o | A sufficiently strong film was formed by baking at 100 to 300° C. Its adhesion to a glass plate was good. | x A film was not formed.
o A sufficiently strong film was formed.
Δ A film was formed, but poor in strength.

EXAMPLE 8

The following adhesion tests were conducted. Every coating solution as indicated in Table 2 was coated on the surfaces of a silicon dioxide substrate and a copper plate by means of a spinner, followed by baking at 200° C. for one hour, to form, respective coated films of 1 to 2 μm in thickness. Each coated film was subjected to such cutting as to form cut lines dividing the film into a number of squares of 2 mm in length of a side thereof. A cellophane adhesive tape was pressed to adhere to the surfaces of the squares, followed by immediate stripping-off of the tape solution. The number of squares stripped off together with the tape from the substrate or plate was counted, and expressed in terms of the number thereof per 100 original squares. The results are shown in Table 2.

TABLE 2

| Run No. | Coating Solution | Kind of Substrate Silicon Dioxide | Copper |
|---|---|---|---|
| 1 | Example 1 | 0 | 87 |
| 2 | Example 6 | 0 | 0 |
| 3 | Comparative Example 3 °1 | 100 | 100 |

°1: A solution of a conventional precursor of polyimide (polyamic acid solution) prepared by reacting an equimolar mixture of pyromellitic dianhydride and diaminodiphenyl ether in N—methyl-2-pyrrolidone, Solids Content: 15% by weight, Inherent Viscosity: 0.82 dl/g measured in the aforementioned manner.

what is claimed is:

1. A soluble imide oligomer having an inherent viscosity (n inh) of 0.05 to 0.5 dl/g as determined by the following equation:

$$\eta \text{ inh} = \frac{\ln \eta/\eta_0}{C}$$

wherein $\eta$ is a value as measured using an Ubbellohde viscometer at an oligomer concentration of 0.5 g/dl in N-methyl-2-pyrrolidone at a temperature of 30±0.01° C., $\eta_0$ is a value for N-methyl-2-pyrrolidone as measured using the same viscometer as described above at the same temperature as described above, and C represents said oligomer concentration of 0.5 g/dl; and represented by the following general formula (I):

wherein $R^1$ and $R^6$ are tetravalent and trivalent carbocyclic aromatic groups, respectively, carbonyl groups being bonded to said carbocyclic aromatic groups at the mutually different ring-forming carbon atoms thereof, every pair of imide ring-forming carbonyl groups being bonded to a carbocyclic ring of said carbocyclic aromatic groups in the mutual ortho positions thereof; $R^2$, $R^3$ and $R^8$, which are the same or different groups; are wherein s is an integer of 1 to 4; $R^4$, $R^5$ and $R^7$, which are the same or different groups, are an alkyl group having 1 to 6 carbon atoms, a phenyl group, or an alkyl-substituted phenyl group having 7 to 12 carbon atoms; R is hydrogen or alkyl or acetyl group; m and n each are an integer of 1, 2 or 3, and satisfy an equation: $m+n \geq 3$; r is 2 or 3; p and q are integers and satisfy the relation of $m+n \leq p < 2(m+n)-1$ and $r \leq q < 2r-1$; t is 0 or 2; and x and y are values satisfying the following equation:

$$0 \leq \frac{100 y}{x+y} \leq 10.$$

2. A soluble imide oligomer as claimed in claim 1, wherein x and y are values satisfying the following equation:

$$0.1 \leq \frac{100 y}{x+y}.$$

3. A soluble imide oligomer as claimed in claim 1, wherein $R^1$ is

4. A soluble imide oligomer as claimed in claim 1, wherein $R^6$ is

5. A soluble imide oligomer as claimed in claim 1, wherein $R^2$, $R^3$ and $R^8$ each are

6. A soluble imide oligomer as claimed in claim 1 wherein $R^4$, $R^5$ and $R^7$ each are —$CH_3$, —$C_2H_5$, or

7. A process for preparing a soluble imide oligomer having an inherent viscosity ($\eta$ inh) of 0.05 to 0.5 dl/g as determined by the following equation:

$$\eta \text{ inh} = \frac{\ln \eta/\eta_0}{C}$$

wherein $\eta$ is a value as measured using an Ubbellohde viscometer at an oligomer concentration of 0.5 g/dl in N-methyl-2-pyrrolidine at a temperature of $30\pm0.01°$ C., $\eta_0$ is a value for N-methyl-2-pyrrolidone as measured using the same viscometer as described above at the same temperature as described above, and C represents said oligomer concentration of 0.5 g/dl; and represented by the following general formula (I):

which process comprises reacting an amic acid compound represented by a general formula (II) mentioned below, or a mixture thereof with 10% by mole or less of an amic acid compound represented by a general formula (III) mentioned below, in the presence of 70% by weight or more, based on a solution, of a solvent, at a temperature of $60°-200°$ C. for $0.2 \sim 6$ hours, wherein $R^1$ and $R^6$ are tetravalent and trivalent carbocyclic aromatic groups, respectively, carbonyl groups being bonded to said carbocyclic aromatic groups at the mutually different ring-forming carbon atoms thereof, every pair of imide ring-forming carbonyl groups being bonded to a carbocyclic ring of said carbocyclic aromatic groups in the mutual ortho positions thereof; $R^2$, $R^3$ and $R^8$, which are the same or different groups are wherein s is an integer of 1 to 4; $R^4$, $R^5$ and $R^7$, which are the same or different groups, are an alkyl group having 1 to 6 carbon atoms, a phenyl group, or an alkyl-substituted phenyl group having 7 to 12 carbon atoms; X is an alkoxyl group, an acetoxyl group, a halogen atom, or a hydroxyl group; R is hydrogen or alkyl or acetyl group derived from X; m and n each are an integer of 1, 2 or 3; and satisfy an equation: $m+n \geq 3$; r is 2 or 3; p and q are integers and satisfy the relation of $m+n \leq p < 2(m+n) - 1$ and $r \leq q < 2r - 1$; t is 0 or 2; and x and y are values satisfying the following equation:

$$0 \leq \frac{100 y}{x + y} \leq 10.$$

8. A process for preparing a soluble imide oligomer as claimed in claim 7, wherein $R^1$ is 9. A process for preparing an soluble imide oligomer as claimed in claim 7, wherein $R^6$ is 10. A process for preparing a soluble imide oligomer as claimed in claim 7, wherein $R^2$, $R^3$ and $R^8$ each are 11. A process for preparing a solution imide oligomer as claimed in claim 7, wherein $R^4$, $R^5$ and $R^7$ each are $-CH_3$, $-C_2H_5$, or 12. A process for preparing a soluble imide oligomer as claimed in claim 7, wherein said solvent includes 30 to 100% by weight of at least one member selected from the group consisting of N-methyl-2-pyrrolidone, dimethylacetamide, dimethylformamide, toluene, xylene, ethylene glycolmonomethyl ether, and dimethyl sulfoxide.

13. A process for preparing a soluble imide oligomer having an inherent viscosity ($\eta$ inh) of 0.05 to 0.5 dl/g as determined by the following equation:

$$\eta \text{ inh} = \frac{\ln \eta/\eta_0}{C}$$

wherein $\eta$ is a value as measured using an Ubbellohde viscometer at an oligomer concentration of 0.5 g/dl in N-methyl-2-pyrrolidone at a temperature of $30 \pm 0.01°$ C., $\eta_0$ is a value for N-methyl-2-pyrrolidone as measured using the same viscometer as described above at the same temperature as described above, and C represents said oligomer concentration of 0.5 g/dl; and represented by the following general formula (I):

which process comprises reacting an amic acid compound represented by a general formula (II) mentioned below, or a mixture thereof with 10% by mole or less of an amic acid compound represented by a general formula (III) mentioned below, in the presence of 70% by weight or more, based on a solution, of a solvent, at a temperature of $60° \sim 200°$ C. for $0.2 \sim 6$ hours, and, in the additional presence of $\{(m+n-2)x + (r-1)y\}$ mole or less per mole of said amic acid compound of water at a temperature of 60° to 200° C. for 0.2 to 6 hours;

wherein $R^1$ and $R^6$ are tetravalent and trivalent carbocylic aromatic groups, respectively, carbonyl groups being bonded to said carbocyclic aromatic groups at the mutually different ring-forming carbon atoms thereof, every pair of imide ring-forming carbonyl groups being bonded to a carbocyclic ring of said carbocyclic aromatic groups in the mutual ortho positions thereof; $R^2$, $R^3$ and $R^8$, which are the same or different groups, are wherein s is an integer of 1 to 4; $R^4$, $R^5$ and $R^7$, which are the same or different groups, are an alkyl group having 1 to 6 carbon atoms, a phenyl group, or an alkyl-substituted phenyl group having 7 to 12 carbon atoms;

X is an alkoxy group, an acetoxyl group, a halogen atom, or a hydroxyl group; m and n each are an integer of 1, 2 or 3, and satisfy an equation: $m+n \geq 3$; r is 2 or 3; p and q are integers and satisfy the relation of $m+n \leq p < 2(m+1)-1$ and $r \leq q < 2r-1$; t is 0 or 2; and x and y are values satisfying the following equation:

$$0 \leq \frac{100y}{x+y} \leq 10.$$

14. A process for preparing a soluble imide oligomer as claimed in claim 13, wherein $R^1$ is

15. A process for preparing a soluble imide oligomer as claimed in claim 13, wherein $R^6$ is 16. A process for preparing a soluble imide oligomer as claimed in claim 13, wherein $R^2$, $R^3$ and $R^8$ each are 17. A process for preparing a soluble imide oligomer as claimed in claim 13, wherein $R^4$, $R^5$ and $R^7$ each are —CH$_3$, —C$_2$H$_5$, or 18. A process for preparing a soluble imide oligomer as claimed in claim 13, wherein said solvent includes 30 to 100% by weight of at least one member selected from the group consisting of N-methyl-2-pyrrolidone, dimethylacetamide, dimethylformamide, toluene, xylene, ethylene glycolmonomethyl ether, and dimethyl sulfoxide.

19. A coating solution for electronic materials comprising a solvent, and 30% by weight or less (based on the total of said solvent and the following soluble imide oligomer), a soluble imide oligomer having an inherent viscosity ($\eta$ inh) of 0.05 to 0.5 dl/g as determined by the following equation:

$$\eta \text{ inh} = \frac{\ln \eta/\eta_0}{C}$$

wherein $\eta$ is a value as measured using an Ubbellohde viscometer at an oligomer concentration of 0.5 g/dl in N-methyl-2-pyrrolidone at a temperature of $30\pm0.01°$ C., $\eta_0$ is a value for N-methyl-2-pyrrolidone as measured using the same viscometer as described above at the same temperature as described above, and C represents said oligomer concentration of 0.5 g/dl; and represented by the following general formula (I):

wherein $R^1$ and $R^6$ are tetravelent and trivalent carbocyclic aromatic groups, respectively, carbonyl groups being bonded to said carbocyclic aromatic groups at the mutually different ring-forming carbon atoms thereof, every pair of imide ring-forming carbonyl groups being bonded to a carbocyclic ring of said carbocyclic aromatic groups in the mutual ortho positions thereof; $R^2$, $R^3$ and $R^8$, which are the same or different groups, are wherein s is an integer of 1 to 4; $R^4$, $R^5$ and $R^7$, which are the same or different groups, are an alkyl group having 1 to 6 carbon atoms, a phenyl group, or an alkyl-substituted phenyl group having 7 to 12 carbon atoms; R is hydrogen or alkyl or acetyl group; m and n each are an integer of 1, 2 or 3, and satisfy an equation: $m+n \geq 3$; r is 2 or 3; p and q are integers and satisfy the relation of $m+n \leq p < 2(n+1)$ and $r \leq q < 2r+1$; t is 0 or 2; and x and y are values satisfying the following equation:

$$0 \leq \frac{100y}{x+y} \leq 10.$$

20. A coating solution for electronic materials as claimed in claim 19, wherein x and y satisfy the following equation:

$$0.1 \leq \frac{100y}{x+y}.$$

21. A coating solution for electronic materials as claimed in claim 19, wherein $R^1$ is 22. A coating solution for electronic materials as claimed in claim 19, wherein $R^6$ is 23. A coating solution for electronic materials as claimed in claim 19, wherein $R^2$, $R^3$ and $R^8$ each are 24. A coating solution for electronic materials as claimed in claim 19, wherein $R^4$, $R^5$ and $R^7$ each are —$CH_3$, —$C_2H_5$ or 25. A coating solution for electronic materials as claimed in claim 19, wherein said solvent includes 30 to 100% by weight of at least one member selected from the group consisting of N-methyl-2-pyrrolidone, dimethylacetamide, dimethylformamide, toluene, xylene, ethylene glycolmonomethyl ether, ethylene glycolmonoethyl ether, and dimethyl sulfoxide.

* * * * *